US007244703B2

(12) United States Patent
Gyurik et al.

(10) Patent No.: US 7,244,703 B2
(45) Date of Patent: *Jul. 17, 2007

(54) PHARMACEUTICAL COMPOSITIONS AND METHODS FOR PEPTIDE TREATMENT

(75) Inventors: Robert J. Gyurik, Exeter, NH (US); Carl Reppucci, North Andover, MA (US)

(73) Assignee: Bentley Pharmaceuticals, Inc., Exeter, NH (US)

( * ) Notice: Subject to any disclaimer, the term of this patent is extended or adjusted under 35 U.S.C. 154(b) by 50 days.

This patent is subject to a terminal disclaimer.

(21) Appl. No.: 10/895,465

(22) Filed: Mar. 5, 2004

(65) Prior Publication Data

US 2005/0232867 A1 Oct. 20, 2005

Related U.S. Application Data

(63) Continuation-in-part of application No. 10/481,309, filed as application No. PCT/US02/19849 on Jun. 24, 2002.

(60) Provisional application No. 60/300,293, filed on Jun. 22, 2001.

(51) Int. Cl.
*A61K 38/02* (2006.01)
*A61K 91/07* (2006.01)

(52) U.S. Cl. .......................................... 514/2; 514/937

(58) Field of Classification Search ..................... None
See application file for complete search history.

(56) References Cited

U.S. PATENT DOCUMENTS 4,211,766 A 7/1980 Bjorklund ................ 424/277.1
4,603,120 A * 7/1986 Kamber ....................... 514/11
4,613,500 A 9/1986 Suzuki et al. ................. 429/85
4,659,696 A * 4/1987 Hirai et al. ................... 514/15
4,755,534 A 7/1988 Stuetz ........................ 514/655
4,760,096 A 7/1988 Sakai et al. ................. 514/847
4,894,375 A 1/1990 Gadebusch et al. ......... 514/249
4,920,109 A 4/1990 Onishi et al. ............... 514/171
4,920,112 A 4/1990 Onishi et al. ............... 514/171
4,957,730 A 9/1990 Bohn et al. ................... 424/61
4,983,393 A 1/1991 Cohen et al. ............... 424/430
5,023,252 A 6/1991 Hseih ......................... 514/183
5,028,431 A 7/1991 Franz et al. ................ 424/449
5,057,312 A 10/1991 Langla et al. ................. 424/81
5,069,906 A 12/1991 Cohen et al. ............... 424/430
5,106,878 A 4/1992 Guerry et al. .............. 514/651
5,116,603 A 5/1992 Friedman ..................... 424/53
5,120,530 A 6/1992 Ferro et al. ................... 424/61
5,132,459 A 7/1992 Stuetz ........................ 564/387
5,160,737 A 11/1992 Friedman et al. ........... 424/401
5,179,079 A * 1/1993 Hansen et al. ................. 514/4
5,214,046 A 5/1993 Guerry et al. .............. 514/255
5,262,150 A 11/1993 Laugier et al. ............... 424/47
5,281,580 A * 1/1994 Yamamoto et al. ........... 514/12
5,292,777 A 3/1994 DesMarais et al. ........... 521/64
5,437,272 A 8/1995 Fuhrman ............... 128/203.12
5,490,498 A 2/1996 Faithfull et al. ....... 128/203.12
5,514,670 A 5/1996 Friedman et al. .............. 514/2
5,540,225 A 7/1996 Schutt .................. 128/207.15
5,562,608 A 10/1996 Sekins et al. ................. 604/20
5,614,171 A 3/1997 Clavenna et al. ............. 424/45
5,618,516 A 4/1997 Clavenna et al. ............. 424/45
5,660,839 A 8/1997 Allec et al. ................. 424/401
5,661,170 A 8/1997 Chodosh ..................... 514/390
5,667,809 A 9/1997 Trevino et al. ............. 424/501
5,681,849 A 10/1997 Richter et al. .............. 514/481
5,696,164 A 12/1997 Sun et al. ................... 514/562
5,719,192 A 2/1998 De Simone et al. ........ 514/655
5,731,303 A * 3/1998 Hsieh ......................... 514/183
5,733,877 A 3/1998 Sato et al. .................... 514/12
5,807,890 A 9/1998 Yu et al. ...................... 514/574
5,813,416 A 9/1998 Rudolph .................... 132/76.4
5,814,305 A 9/1998 Laugier et al. ............... 424/61
5,817,875 A 10/1998 Karimian et al. ........... 564/387
5,837,289 A 11/1998 Grasela et al. .............. 424/484
5,840,283 A 11/1998 Sorenson et al. ............. 424/61
5,856,355 A 1/1999 Richter et al. .............. 514/481
5,866,105 A 2/1999 Richter et al. ................ 424/61
5,898,028 A 4/1999 Jensen et al. .................. 514/4
5,902,789 A * 5/1999 Stoltz ........................... 514/4
5,908,824 A 6/1999 Yanagawa ...................... 514/2
5,919,757 A 7/1999 Michaelis et al. ............. 514/8
5,925,616 A 7/1999 Whittemore ................... 514/2

(Continued)

FOREIGN PATENT DOCUMENTS

EP 0156507 10/1985

(Continued)

OTHER PUBLICATIONS

Aungst et al. Site Dependence of Absorption-Promoting Actions of Laureth-9 . . . Pharmaceutical Research. 1988, vol. 5, No. 5, pp. 305-308.*

(Continued)

*Primary Examiner*—Jeffrey Edwin Russel
(74) *Attorney, Agent, or Firm*—Elliot M. Olstein; Raymond E. Stauffer

(57) ABSTRACT

Compositions and methods for treating a patient with a pharmaceutically active peptide that combines a pharmaceutically active peptide, a permeation enhancer, and a carrier, are disclosed.

16 Claims, No Drawings

U.S. PATENT DOCUMENTS

| | | | | |
|---|---|---|---|---|
| 5,935,998 | A | 8/1999 | Lindley et al. | 514/481 |
| 5,942,545 | A | 8/1999 | Samour et al. | 514/573 |
| 5,945,409 | A | 8/1999 | Crandall | 514/78 |
| 5,968,919 | A | 10/1999 | Samour et al. | 514/177 |
| 5,976,547 | A | 11/1999 | Archer et al. | 424/742 |
| 5,976,566 | A | 11/1999 | Samour et al. | 424/449 |
| 5,985,906 | A | 11/1999 | Meingassner et al. | 514/383 |
| 5,993,787 | A | 11/1999 | Sun et al. | 424/59 |
| 6,005,001 | A | 12/1999 | Richter et al. | 514/481 |
| 6,017,920 | A | 1/2000 | Kamishita et al. | 514/252 |
| 6,024,976 | A | 2/2000 | Miranda et al. | 424/449 |
| 6,030,948 | A | 2/2000 | Mann | 514/12 |
| 6,121,314 | A | 9/2000 | Richter et al. | 514/481 |
| 6,136,332 | A | 10/2000 | Grollier et al. | 424/404 |
| 6,142,155 | A | 11/2000 | Rudolph | 132/76.4 |
| 6,143,793 | A | 11/2000 | Laugier et al. | 514/655 |
| 6,165,484 | A | 12/2000 | Raad et al. | 424/405 |
| 6,190,690 | B1 | 2/2001 | Park et al. | 424/449 |
| 6,207,142 | B1 | 3/2001 | Odds et al. | 424/70.8 |
| 6,207,703 | B1 | 3/2001 | Ponikau | 514/460 |
| 6,214,360 | B1 | 4/2001 | Richter et al. | 424/401 |
| 6,221,383 | B1 | 4/2001 | Miranda et al. | 424/449 |
| 6,224,887 | B1 | 5/2001 | Samour et al. | 424/401 |
| 6,225,075 | B1 | 5/2001 | Bard | 435/15 |
| 6,231,875 | B1 | 5/2001 | Sun et al. | 424/401 |
| 6,242,509 | B1 | 6/2001 | Berger et al. | 523/122 |
| 6,267,979 | B1 | 7/2001 | Raad et al. | 424/405 |
| 6,291,500 | B2 | 9/2001 | Ponikau | 514/393 |
| 6,294,192 | B1 | 9/2001 | Patel et al. | 424/451 |
| 6,294,350 | B1 | 9/2001 | Peterson | 435/29 |
| 6,319,509 | B1 | 11/2001 | Richter et al. | 424/401 |
| 6,328,728 | B1 | 12/2001 | Holladay et al. | 604/501 |
| 6,335,023 | B1 | 1/2002 | Yu et al. | 424/401 |
| 6,380,236 | B2 | 4/2002 | Glassman | 514/399 |
| 6,383,471 | B1 | 5/2002 | Chen et al. | 424/45 |
| 6,383,523 | B1 | 5/2002 | Murad | 424/616 |
| 6,399,571 | B1 | 6/2002 | Gray et al. | 514/12 |
| 6,403,063 | B1 | 6/2002 | Sawyer | 424/61 |
| 6,433,040 | B1 | 8/2002 | Dellamary et al. | 523/218 |
| 6,455,592 | B1 | 9/2002 | Laugier et al. | 514/655 |
| 6,479,532 | B1 | 11/2002 | Kamimura et al. | 514/397 |
| 6,482,839 | B1 | 11/2002 | Thornfeldt | 514/345 |
| 6,485,706 | B1 | 11/2002 | McCoy et al. | 424/45 |
| 6,495,124 | B1 | 12/2002 | Samour | 424/61 |
| 6,503,953 | B2 | 1/2003 | Vyden | 514/741 |
| 6,509,319 | B1 | 1/2003 | Raad et al. | 514/31 |
| 6,514,490 | B2 | 2/2003 | Odds et al. | 424/70.8 |
| 6,515,181 | B2 | 2/2003 | Castaldi et al. | 564/387 |
| 6,531,126 | B2 | 3/2003 | Farmer | 424/115 |
| 6,555,566 | B2 | 4/2003 | Ponikau | 514/393 |
| 6,569,463 | B2 | 5/2003 | Patel et al. | 424/497 |
| 6,585,967 | B2 | 7/2003 | Narang et al. | 424/78.31 |
| 6,596,267 | B1 | 7/2003 | Hubbell et al. | 424/78.26 |
| 6,596,325 | B1 | 7/2003 | Vroom | 424/769 |
| 6,602,496 | B2 | 8/2003 | Hedgpeth et al. | 424/78.07 |
| 6,604,698 | B2 | 8/2003 | Verhoff et al. | 241/21 |
| 6,623,732 | B1 * | 9/2003 | Ma | 424/85.4 |
| 6,623,753 | B1 | 9/2003 | Bodmer et al. | 424/450 |
| 6,645,506 | B1 | 11/2003 | Farmer | 424/260.1 |
| 6,645,528 | B1 | 11/2003 | Straub et al. | 424/489 |
| 6,673,054 | B1 | 1/2004 | Gould et al. | 604/292 |
| 6,673,369 | B2 | 1/2004 | Rampal et al. | 424/468 |
| 6,680,308 | B1 | 1/2004 | Hassan | 514/125 |
| 6,688,304 | B2 | 2/2004 | Gonda et al. | 128/200.14 |
| 6,689,913 | B2 | 2/2004 | Lee et al. | 564/337 |
| 6,689,986 | B2 | 2/2004 | Patel et al. | 219/121.71 |
| 6,694,975 | B2 | 2/2004 | Schuster et al. | 128/203.26 |
| 6,849,263 | B2 | 2/2005 | Modi | 424/400 |
| 6,878,365 | B2 | 4/2005 | Brehove | 424/61 |
| 6,899,890 | B2 | 5/2005 | Kirschner et al. | 424/430 |
| 6,914,051 | B1 | 7/2005 | Allen | 514/29 |
| 6,956,058 | B2 | 10/2005 | Hase et al. | 514/547 |
| 6,958,142 | B2 * | 10/2005 | Daniels et al. | 424/45 |
| 6,967,192 | B2 | 11/2005 | Oeltgen et al. | 514/12 |
| 2001/0055569 | A1 | 12/2001 | Davis et al. | 424/43 |
| 2002/0123437 | A1 | 9/2002 | Conboy et al. | 510/101 |
| 2002/0165155 | A1 | 11/2002 | Schaffer et al. | 514/12 |
| 2003/0049307 | A1 | 3/2003 | Gyurik | 424/449 |
| 2003/0086881 | A1 | 5/2003 | Bohn et al. | 424/61 |
| 2003/0188679 | A1 | 10/2003 | Schwarz et al. | 117/2 |
| 2003/0211995 | A1 * | 11/2003 | Kokai-Kun et al. | 514/12 |
| 2003/0229010 | A1 | 12/2003 | Ekwuribe | 514/3 |
| 2004/0077540 | A1 * | 4/2004 | Quay | 514/12 |
| 2004/0167203 | A1 | 8/2004 | Chang et al. | 514/440 |
| 2004/0176476 | A1 | 9/2004 | Gyurik | 514/772.6 |
| 2004/0197280 | A1 | 10/2004 | Repka | 424/61 |
| 2004/0235956 | A1 | 11/2004 | Quay | 514/573 |
| 2005/0032683 | A1 | 2/2005 | Amento et al. | 514/12 |
| 2005/0069578 | A1 | 3/2005 | Balasubramanian | 424/450 |
| 2005/0143303 | A1 * | 6/2005 | Quay et al. | 514/12 |
| 2005/0215477 | A1 | 9/2005 | Schaffer et al. | 514/12 |

FOREIGN PATENT DOCUMENTS

| | | |
|---|---|---|
| EP | 0226984 | 7/1987 |
| EP | 0298271 | 1/1989 |
| EP | 0325949 | 8/1989 |
| EP | 0385952 | 9/1990 |
| EP | 0399858 | 11/1990 |
| EP | 0472858 | 3/1992 |
| EP | 0478456 | 4/1992 |
| EP | 0503988 | 9/1992 |
| FR | 2265357 | 10/1975 |
| GB | 2002795 | 2/1979 |
| GB | 2098865 | 12/1982 |
| GB | 2148711 | 6/1985 |
| GB | 2197194 | 5/1988 |
| WO | WO 87/02580 | 5/1987 |
| WO | WO 88/06884 | 9/1988 |
| WO | WO 96/35423 | 11/1996 |
| WO | WO 97/02026 | 1/1997 |
| WO | WO 99/59543 | 11/1999 |
| WO | WO 99/59543 A1 * | 11/1999 |
| WO | WO 03/000158 | 1/2003 |
| WO | WO 03/088974 | 10/2003 |
| WO | WO 2005/056038 | 6/2005 |

OTHER PUBLICATIONS

"Correlations between Secondary Ion Intensity . . . ". Rapid Communications in Mass Spectrometry. 1995, vol. 9, pp. 541-549.*

Aungst et al., Site Dependence of Absorption-Promoting Actions of Laureth-9, Na Salicylate, $Na_2EDTA$, and Aprotinin on Rectal, Nasal, and Buccal Insulin Delivery, Pharmaceutical Research, vol. 5, No. 5, pp. 305-308, Jan. 2, 1988.

Gallo et al., Allergic Contact Dermatitis From Laureth-9 and Polyquaternium-7 in a Skin-Care Product, Contact Dermatitis, vol. 45, No. 6, Dec. 2001.

Hirai et al., Nasal Absorption of Insulin in Dogs, Diabetes, vol. 27, No. 3, pp. 296-298, Mar. 1978.

Jones, Treatment of Dermatomycoses with Topically Applied Allylamines: Naftifine and Terbinafine, Journal of Dermatological Treatment, 1990, pp. 29-32.

Kokai-Kun et al., Lysostaphin Cream Eradicates *Staphylococcus aureus* Nasal Colonization in a Cotton Rat Model, Antimicrob Agents Chemother. May 2003; 47(5): 1589-97, (Abstract only).

Leary et al., Pharmacokinetics and Pharmacodynamics of Intranasal Insulin Administered to Healthy Subjects in Escalating Doses, Diabetes Technol. Ther. Feb. 2005;7(1):124-30 (Abstract).

Leary et al., Pharmacokinetics and Pharmacodynamics of Intranasal Insulin Administered to Patients with Type 1 Diabetes: A Preliminary Study, Diabetes Technology & Therapeutics vol. 8, No. 1, 2006.

Leary et al., Intranasal Insulin Administration in Normal Subjects Utilizing CPE-215® Technology, (Abstract No. Lear 4167 and Poster), Diabetes Technology Meeting in Philadelphia, PA, Oct. 28-30, 2004.
Leary et al., Intranasal Insulin Administration in Type 1 Diabetic Patients Utilizing CPE-215® Technology, (Abstract No. Lear 952997 and Poster), American Diabetes Association Meeting in San Diego, CA, Jun. 9-14, 2005.
Lochhead et al., Hydrophobically Modified "Carbopol" Resins, Soap/Cosmetics/Chemical Specialities for May, 1987, pp. 28-33.
Mort, Multiple Modes of Drug Delivery, Technologies such as microchips and microspheres are enabling the therapeutic use of proteins, Modern Drug Discovery, Apr. 2000, 3(3) 30-32, 34.
Patton, Deep-Lung Delivery of Therapeutic Proteins, Chemtech, Dec. 1997, Chemtech 1997, 27(12), 34-38.
Paulsen, Contact Sensitization From Compositae-Containing Herbal Remedies and Cosmetics, Contact Dermatitis, Oct. 2002;47(4): 189-98, (Abstract only).
Petranyi et al., Activity of Terbinafine in Experimental Fungal Infections of Laboratory Animals, Antimicrobial Agents and Chemotherapy, Oct. 1987, p. 1558-1561.
Savin, Successful Treatment of Chronic *Tinea pedis* (moccasin type) With Terbinafine (Lamisil), Clinical and Experimental Dermatology 1989; 14: 116-119.
Spettoli et al., Contact Dermatitis Caused by *Sesquiterpene lactones*, Am J Contac Dermat. Mar. 1998; 9(1): 49-50. (Abstract only).
Taylor et al., Structural Studies of Phycobilliproteins From Spirulina: Combining Spectroscopy, Thermodynamics, and Molecular Modeling in an Undergraduate Biochemistry Experiment, Journal of Chemical Education, vol. 79, No. 12, pp. 1467-1470, Dec. 2002.
Villars et al., Present Status of the Efficacy and Tolerability of Terbinafine (Lamisil) Used Systemically in the Treatment of Dermatomycoses of Skin and Nails, Journal of Dermatological Treatment (1990), 1, Suppl. 2, 33-38.
Willimann et al., Lecithin Organogel as Matrix for Transdermal Transport of Drugs, Journal of Pharmaceutical Sciences, vol. 81, No. 9, pp. 871-874, Sep. 1992.
Young et al., Histoplasmosis and HIV Infection, HIV InSita Knowledge Base Chapter, May 2005.
About MEROPS, Classification: Three Orthogonal Approaches, (2005).
Ammonium Thioglycolate, Haz Map, Occupational Exposure to Hazardous Agents, (2004).
Bachem AG, Myelin Basic Protein Fragments, H-2680, H-3584, H-1072, H-3238, H-6870, H-6875, H-4306, H-1964, H-3392, H-6022 and Peptides H-9435, H-5806, H-3046, H-2155, H-3914, H9855, H8090, H2665, H-6405, H-4864, H-4766, H2758, H3845, H-3424, H-6022, H-1964, H-4585, H-3022, H-2926, H-9195, H-5035, H-2698, and H-3775, Not dated.
Cyclooctane, CDN Isotopes, Material Safety Data Sheet, Sheet No. 3440, (2004).
Endopeptidases, General Practice Notebook, not dated.
Isopropyl Myristate, RITA Your Source for Specialty Chemicals, (1997).
Isopropyl Myristate, ChemExper Chemical Directory, Catalog of Chemicals and Suppliers, not dated.
Lauric acid sodium salt, RN: 629-25-4, not dated.
Limonene, International Programme On Chemical Safety, Concise International Chemical Assessment Document No. 5, not dated.
Lyso PC, Cayman Chemical, (2006).
The Merck Index, An Encyclopedia of Chemicals, Drugs, and Biologicals, Twelfth Edition, pp. 128, 551, 813, 814, 938, 1302, 1308, and 1483, (1996).
Mono Decanoyl Octanoyl Glyceride, HUDONG Household Auxilliaries, not dated.
N-Decanoic Acid Sodium Salt MSDS, Material Safety Data Sheet, Science lab.com, (2005).
Nonoxynol-9, Wikipedia the free encyclopedia, (2006).
Phosphatidylcholine, PDR Health, not dated.
Polidocanol (Thesit), Roche Applied Science 2005/2006.
Polysorbate 80, Ingredients, Chemical Formula, not dated.
Preparation of Food Contact Notifications and Food Additive Petitions for Food Contact Substances: Chemistry Recommendations, U.S. Food and Drug Administration, CFSAN/Office of Food Additive Safety, Apr. 2002.
Safety (MSDS) Data For Lauric Acid Sodium Salt, (2003).
Sodium Glycocholate MSDS, Material Safety Data Sheet, Science Lab.com, (2005).
Sodium Myristate, Viva, not dated.
Sodium Sulfide, $Na_2S$ $9H_2O$, Reagent Grade, ACS Specifications, Processing KODAK Motion Picture Films, Module 4, not dated.
Sodium Sulfide, Material Safety Data Sheet, MSDS No. S5042, (2003).
Sodium Taurocholate MSDS, Material Safety Data Sheet, Science Lab.com, (2005).
Taurine, Substance Summary, National Library of Medicine, PubChem, not dated.
Taurine (2-Aminoethylsulfonic Acid), Changshu Jincheng Chemical Factory, Jincheng Chemicals, (2004).
Taurocholic Acid, The Comparative Toxicogenomics Database, (2006).
The Safety of Sporanox Capsules and Lamisil Tablets For the Treatment of Onychomycosis, FDA Public Health Advisory, CDER, Drug Information, (2001).
Topical Formulation Optimisation For Perungual Drug Delivery, MedPharm, not dated.
Universal Preserv-A-Chem, Inc., Products, not dated.
Urea, Material Safety Data Sheet According to 91/155 EEC, Promega, (2004).
Ursodeoxycholic Acid, The Comparative Toxicogenomics Database, (2006).
Baker, Roche Files Lawsuit Against Schering-Plough for Patent Infringement of Roche's "PEG" Interferon, HIV and Hepatitis.com, Jan. 10, 2000.
Kurmaev et al., Probing oxygen and nitrogen bonding sites in chitosan by X-ray emission, Journal of Electron Spectroscopy and Related Phenomena, 125 133-138, (2002).
Porras et al., Studies of formation of W/O nano-emulsions, Colloids and Surfaces A: Physiochem. Eng. Aspects 249 (2004) 115-118.
Basic Terms Needed to Understand Osmolality, InfinitT Nutrition, LLC. 2006.
Ingredient Definitions: Wanda Embar 2004.
JEECOL CS-20-D Cetearyl Alcohol and CETEARTH 20; JEEN International Corp., not dated.
Polyethylene glycol, Answers.com, Answers Corporation 2006.
Polyethylene glycol, Wikipedia; Jun. 1, 2006.
Polysorbate 20, MSDS Material Safety Data Sheet, From Mallinkrodt Baker, Inc. Nov. 4, 2004.
Sorbitan esters, Danisco 2005 Danisco A/S.
SPAN Series, Xingtai Lantian Fine Chemical Co., Ltd. 2005.
SPAN 20 (=Sorbitan monolaurate), ZIZHU Pharmaceutical (2000).
Tween Series Polyoxyethylene derivatives of sorbitan esters, Uniqema 2004.
Tween 20—Polysorbate 20, Well Naturally Products Ltd., not dated.

* cited by examiner

PHARMACEUTICAL COMPOSITIONS AND METHODS FOR PEPTIDE TREATMENT

This application is a continuation-in-part of U.S. application Ser. No. 10/481,309, filed on Dec. 18, 2003, which is the National Stage Entry of International Application Serial No. PCT/US02/19849 filed Jun. 24, 2002, which claims priority to U.S. Provisional Application Ser. No. 60/300,293 filed Jun. 22, 2001, the disclosures of each of which are hereby incorporated by reference in their entireties.

The present invention relates to a composition useful for drug delivery. More particularly the invention relates to compositions and methods for the delivery of peptide drugs, peptidomimetics, or proteins through the nasal mucosa. The pharmaceutical compositions of the present invention include a permeation enhancer, that is, a material which is capable of increasing the rate of passage of the peptide through the nasal mucosa.

The present invention will be described initially with respect to its use in the intra-nasal delivery of pharmaceutically active peptides. It should be understood, however, that the present invention can also be used for the intranasal delivery of peptidomimetics (synthetic peptides) or proteins.

A peptide is a protein fragment comprising a short chain of amino acids, no less than two amino acids. A protein is generally a longer chain of amino acids, though there is no exact rule as to where a peptide ends and a protein begins. The general peptide/protein nomenclature also considers whether the structure is a whole molecule, such as insulin-like growth factor-1 (IGF-1) that is a 73 amino acids long peptide, or if the structure is a fragment of a protein molecule, such as a trypsin cleaved fragment of a protein that would normally be called a trypsin peptide.

In general, the peptides, peptidomimetics, and proteins used in the present invention have molecular weights on the order of about 100 to about 50,000 daltons. In one embodiment the peptides used in the present invention have molecular weights on the order of about 100 to about 30,000 daltons, though other peptides, which, due to their coiling may be larger than 30,000 daltons, are also within the scope of the invention. In a preferred embodiment the peptides used in the present invention have molecular weights on the order of about 100 to about 10,000 daltons. In a more preferred embodiment the peptides used in the present invention have molecular weights on the order of about 100 to about 7,000 daltons. In one embodiment the peptide is within the more preferred range and it is a peptide other than insulin.

Peptides are used to treat patients suffering from myriad conditions such as osteoporosis, cystic fibrosis, endometriosis, encephalomyelitis, pancreatic disorders, obesity, pain, growth problems, appetite disorders, and sequelae of diabetes. The foregoing are non-limiting examples of just some disorders that the instant invention may be used to treat. While the instant invention may be used to treat acute conditions, it is preferably used to treat chronic conditions. In general, peptides like many proteins are delivered to a patient by injection, owing to the tendency that these macromolecules have to be destroyed by the digestive tract when ingested orally. Injection therapies however have numerous drawbacks such as the discomfort to the patient, poor patient compliance, and the need for administration by trained technicians. There is therefore a need in the art for alternative methods of delivering peptide medications to patients other than by injection.

A desired alternative method of peptide treatment would be the intra-nasal administration of a composition containing pharmaceutically active peptides. This form of administration is more convenient. In addition, certain agents that produce an antigenic effect when administered by injection do not produce an antigenic effect when administered intranasally. The intra-nasal administration of peptides would thus lead to fewer immunological problems for the patient. The present invention includes within its scope the intranasal method of delivering peptides, peptidomimetics, and proteins.

The treatment of patients with compositions in the form of intra-nasal sprays containing pharmaceutically-active compounds has been disclosed in the art. For example, U.S. Pat. No. 5,989,535 discloses an intra-nasal spray which contains insulin. Such intra-nasal sprays, however, have had limited success because various pharmaceutically-active compounds, including, for example, insulin, are not particularly effective in penetrating the mucous membrane of the nasal passage. Historically, effective intra-nasal delivery of peptides has been unachievable because of the peptide's inability to permeate the nasal mucosa and the tendency of some permeation agents to irritate those membranes. The instant invention overcomes both of those prior art problems.

The use of an enhancer to improve the delivery of a pharmaceutically-active compound to a targeted area has been proposed. U.S. Pat. No. 5,023,252 describes a composition for delivery of drugs by a route other than by injection. More particularly, such patent describes the use of compositions that include permeation enhancers for delivery of drugs through skin and membranes of body cavities without requiring an injection.

The present invention is directed to an improvement in such compositions and the use thereof.

In accordance with the invention, there is provided a pharmaceutical composition for treating a patient comprising: (A) a pharmaceutically active peptide; (B) a permeation enhancer; and (C) a liquid carrier wherein the composition is in a form suitable for intranasal delivery thereof and wherein the peptide is present in an amount effective for treating a patient.

The invention further relates to treating a patient in need of a peptide medication with a combination of a pharmaceutically active peptide, a permeation enhancer, and a liquid carrier.

In general, the permeation enhancer that is employed is one that enhances the permeation of the pharmaceutically active peptide composition through the nasal mucosa.

In a composition containing an effective amount of a pharmaceutically active peptide a preferred permeation enhancer is a compound of the structure:

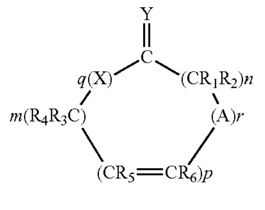

wherein X and Y are oxygen, sulfur or an imino group of the structure

or =N—R with the proviso that when Y is the imino group, X is an imino group, and when Y is sulfur, X is sulfur or an imino group, A is a group having the structure

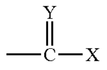

wherein X and Y are defined above, m and n are integers having a value from 1 to 20 and the sum of m+n is not greater than 25, p is an integer having a value of 0 or 1, q is an integer having a value of 0 or 1, r is an integer having a value of 0 or 1, and each of R, $R_1$, $R_2$, $R_3$, $R_4$, $R^5$ and $R^6$ is independently hydrogen or an alkyl group having from 1 to 6 carbon atoms which may be straight chained or branched provided that only one of $R_1$ to $R_6$ can be an alkyl group, with the proviso that when p, q and r have a value of 0 and Y is oxygen, m+n is at least 11, and with the further proviso that when X is an imino group, q is equal to 1, Y is oxygen, and p and r are 0, then m+n is at least 11, and said compound will enhance the rate of the passage of the pharmaceutically active peptide across body membranes. Hereinafter these compounds are referred to as enhancers. When R, $R_1$, $R_2$, $R_3$, $R_4$, $R_5$ or $R_6$ is alkyl it may be methyl, ethyl, propyl, isopropyl, butyl, isobutyl, sec-butyl, amyl, hexyl, and the like. Such permeation enhancers are described in U.S. Pat. Nos. 5,023,252 and 5,731,303.

Preferably, the permeation enhancer compounds of this invention are the cyclic lactones (the compounds wherein both X and Y are oxygen, (q is 1 and r is 0), the cyclic diesters (the compounds wherein both X and Y are oxygen, and both q and r are 1), and the cyclic ketones (the compounds wherein both q and r are 0 and Y is oxygen). In the cyclic diesters m+n is preferably at least 3. In the cyclic ketones m+n is preferably from 11 to 15 and p is preferably 0.

Enhancers of the above structural formula are referred to herein as "Hsieh enhancers" and are described, for example, in aforementioned U.S. Pat. Nos. 5,023,252 and 5,731,303 (hereinafter the "Hsieh Patents"). Such enhancers are lipophilic and are "membrane-compatible," meaning that they do not cause damage to the membrane on which the composition of the present invention is to be applied (hereinafter the "target membrane"). Such enhancers also produce a low level of irritability or no irritability to the target membrane, and in fact serve as emollients.

Preferred enhancers for use in the present invention are macrocyclic enhancers. The term "macrocyclic" is used herein to refer to cyclic compounds having at least 12 carbons in the ring. Examples of preferred macrocyclic enhancers for use in the present invention include: (A) macrocyclic ketones, for example, 3 methylcyclopentadecanone (muscone), 9-cycloheptadecen-1-one (civetone), cyclohexadecanone, and cyclopentadecanone (normuscone); and (B) macrocyclic esters, for example, pentadecalactones such as oxacyclohexadecan-2-one (cyclopentadecanolide, ω-pentadecalactone).

Oxacyclohexadecan-2-one and cyclopentadecanone are especially preferred.

Although the above are preferred permeation enhancers, one of ordinary skill in the art would recognize that the instant teachings would also be applicable to other permeation enhancers. Non-limiting examples of other permeation enhancers useful in the instant invention are the simple long chain esters that are Generally Recognized As Safe (GRAS) in the various pharmacopoeial compendia. These may include simple aliphatic, unsaturated or saturated (but preferably fully saturated) esters, which contain up to medium length chains. Non-limiting examples of such esters include isopropyl myristate, isopropyl palmitate, myristyl myristate, octyl palmitate, and the like. The enhancers are of a type that are suitable for use in a pharmaceutical composition. The artisan of ordinary skill will also appreciate that those materials that are incompatible with or irritating to mucous membranes should be avoided.

The enhancer is present in the composition in a concentration effective to enhance penetration of the pharmaceutically active peptide that is to be delivered through the nasal mucosa. Various considerations should be taken into account in determining the amount of enhancer to use. Such considerations include, for example, the amount of flux (rate of passage through the membrane) achieved and the stability and compatibility of the components in the formulations. The enhancer is generally used in an amount of about 0.1 to about 10 wt. % of the composition, and more generally in an amount of about 1.0 to about 3 wt. % of the composition.

The liquid carrier is present in the composition in a concentration effective to serve as a suitable vehicle for the compositions of the present invention. In general, the carrier is used in an amount of about 40 to about 98 wt. % of the composition and in preferred embodiments in an amount of about 50 to about 98 wt. % of the composition.

The pharmaceutically active peptide compositions of the present invention are preferably delivered as nasal sprays. In such embodiments, the preferred liquid carrier is water with the pharmaceutically active peptide being dispersed or dissolved in the water in a therapeutically effective amount. The water may contain suitable buffering agents to result in a pH wherein the particular peptide is delivered optimally, or it may contain other co-carriers, such as glycerin, propylene glycol, polyethylene glycols of various sizes, amino acid modifiers, such as arginine and the like, and other suitable soluble excipients, as is known to those who are proficient in the art of compounding or pharmaceutics.

As non-limiting examples of peptides useful in the present invention there may be mentioned: Anti-Inflammatory Peptides such Anti-Inflammatory Peptide 1; Anti-Aging Peptides; Apelin Peptides such as Apelin-12; Atrial Natriurectic Peptides such as Urodilatin; Bombesin and Analogs thereof; Brain Injury Derived Peptide; Calcitonin; Defensins; Deltorphins, Dermorphins and Analogs thereof including other opiod peptides such as Acetalins, BAM Peptides, α-Casein Exorphins, β-Casomorphins, Dynorphins, Endomorphins, Endorphins, Enkephalins, Gluten Exorphins, Kyotorphins, Methorphamide, Neoendorphins, Syndyphalins, H-Tyr-D/L-Tic-OH, and Valorphin; Dynorphin and Analogs and Sequences thereof; Enterostatins; GHrelins; Glucagons and Glucagon-Like Peptides such as GLP-1 and GLP-2; Gonadotropin Releasing Hormones; Growth Hormones; Growth Hormone Releasing Hormones; Insulino-Tropic Compounds; Kyotorphins; Leptin and Fragments thereof; Lutein; Myelin Basic Protein Fragments; Physalaemin and Fragments thereof; Secretins; Thymosins and Fragments thereof such as Thymosin β4; Transforming Growth Factors (TGF) and Fragments thereof; Tuftsin; Tumor Necrosis Factors (TNF) and Related Peptides; and VIP, Prepro VIP, and Analogs and Fragments thereof.

The composition of the present invention may exist in various forms, for example, an oil-in-water emulsion, a water-in-oil emulsion, and a water-in-oil-in-water emulsion. The active compounds of the compositions of the present invention may exist in either the continuous or the dispersed phase or in both phases depending upon whether the compounds are hydrophilic, lipophilic, or amphiphilic. In an example of a preferred embodiment of the present invention, the emulsion comprises oil droplets dispersed in a continuous aqueous phase with a lipophilic enhancer being contained in the oil droplets and a water-soluble pharmaceutically-active compound dissolved in the continuous aqueous phase.

The composition of the present invention may also comprise an emulsifying agent for use in aiding the formation of an emulsion. Essentially any suitable hydrocolloid emulsifying agent, typically a solid material, or a mixture of two or more such emulsifying agents can be used in the practice of the present invention. Hydrocolloid emulsifying agents include: vegetable derivatives, for example, acacia, tragacanth, agar, pectin, and carrageenan; animal derivatives, for example, gelatin, lanolin, cholesterol, and lecithin; semi-synthetic agents, for example, methylcellulose and carboxymethylcellulose; and synthetic agents, for example, acrylic emulsifying agents such as carbomers. The hydrocolloid emulsifying agent forms hydrocolloids (hydrated lyophilic colloids) around the emulsified liquid droplets of the emulsion. The hydrocolloid serves as a protective layer around each emulsified droplet which physically repulses other droplets, thus hindering Ostwald ripening (the tendency of emulsified droplets to aggregate). In contrast, other emulsifying agents typically protect the emulsified droplets by forming a liquid crystalline layer around the emulsified droplets. In compositions which employ a liquid crystalline layer-forming emulsifying agent, the hydrophilic-lipophilic balance (HLB) of the oil phase of the emulsion must be matched with that of the emulsifying agent to form a stable emulsion and, often, one or more additional emulsifying agents (secondary emulsifying agents) must be added to further stabilize the emulsion. The aforementioned liquid crystalline layer also retards the release of the compounds of the dispersed phase upon contact with the target substrate.

The hydrocolloid emulsifying agents for use in the composition of the present invention include compounds which exhibit a low level of irritability or no irritability to the target membrane and which have good bioadhesive and mucoadhesive properties. Examples of hydrocolloid emulsifying agents which exhibit such properties include cellulosic emulsifying agents and acrylic emulsifying agents, including, for example, those which have an alkyl group containing from about 10 to about 50 carbon atoms. Particularly preferred acrylic emulsifying agents for use in the present invention are copolymers of a carboxylic acid and an acrylic ester (described, for example, in U.S. Pat. No. 3,915,921 to Schlatzer and U.S. Pat. No. 4,509,949 to Huang et al.), with those which are cross-linked being especially preferred. An example of such an especially preferred emulsifying agent for use in forming an oil-in-water emulsion is "acrylates/$C_{10-30}$ alkyl acrylate crosspolymer", a cross-linked polymer of acrylic acid and ($C_{10-30}$) alkyl acrylates. Acrylates/$Cl_{10-30}$ alkyl acrylate crosspolymer is available from Noveon, Inc. (previously B.F. Goodrich) and is sold under the trade name Pemulen®. Acrylates/$C_{10-30}$ alkyl acrylate crosspolymer has a small lipophilic portion and a large hydrophilic portion, thus allowing for it to function as a primary emulsifier for the formation of oil-in-water emulsions. In addition, acrylates/$C_{10-30}$ alkyl acrylate crosspolymer is capable of releasing the compounds of the dispersed phase upon contact with a substrate, namely, biological membranes or mucosa and will not re-wet (the oil phase will not re-emulsify upon contact with water). Additional information regarding acrylates/$C_{10-30}$ alkyl acrylate crosspolymer, which is listed in the U.S. Pharmacopeia, is provided in Noveon publications TDS-114, 117, 118, 124, 232-3, and 237, and PDS Pemulen 1622.

In forming an emulsion in which the water-insoluble enhancer is a normally solid material, the enhancer is dissolved in a suitable solvent. If the enhancer is a normally liquid material which is water-immiscible, a suitable solvent for the enhancer may or may not be used, as appropriate.

The emulsifying agent is present in the composition in a concentration that is effective to form the desired liquid emulsion. In general the emulsifying agent is used in an amount of about 0.001 to about 5 wt. % of the composition, and more generally in an amount of about 0.01 to about 5 wt. % of the composition, and most generally in an amount of about 0.1 to about 2 wt. % of the composition.

The composition of the present invention may include, as an optional ingredient, particulate solids dispersed in the composition. For example, the composition may include an additional pharmaceutically-active compound dispersed in the liquid continuous phase of the emulsion in the form of microcrystalline solids or nanoparticulates.

While the hydrocolloid emulsifying agent forms a protective layer around the emulsified liquid droplets, thus forming a stable emulsion by hindering Ostwald-ripening without the need for further stabilizing agents, in some instances it may be desirable to further improve the stability of the emulsion. Such may be accomplished by the addition of Ostwald-ripening inhibitors and/or surfactants.

An Ostwald-ripening inhibitor is a material which reduces the tendency of emulsified droplets to aggregate and form larger droplets. Essentially any suitable Ostwald-ripening inhibitor or a mixture of such inhibitors may be used to improve further the physical stability of the emulsion. Preferred Ostwald-ripening inhibitors are hydrophobic agents such as hydrocarbons and hydrocarbon waxes. Examples of hydrophobic agents are petrolatum, hexadecane, and long-chain esters, for example, octyl palmitate. The Ostwald-ripening inhibitor is present in the composition in a concentration effective to prevent the emulsified droplets, particularly relatively small droplets (for example, one micron in diameter), from aggregating into larger droplets which may result in settling (materials settling to the bottom) or creaming (oils rising to the top). For guideline purposes, it is believed most applications will involve the use of the Ostwald-ripening inhibitor in an amount of about 0.001 to about 5 wt. % of the composition and more likely in an amount of about 0.1 to about 1 wt. % of the composition.

In one preferred embodiment, the permeation enhancer is emulsified in the aqueous phase that contains the pharmaceutically active peptide. The emulsification may be effected through the use of one or more suitable surfactants. The selection of a suitable surfactant is deemed to be within the scope of those skilled in the art based on the teachings herein. Such surfactants include for example, anionic, cationic, and non-ionic surfactants. Preferred surfactants are non-ionic surfactants. Alone or in combination with one or more other surfactants, those having a hydrophilic-lipophilic balance number (HLB) of from about 4 to about 18 are preferred, those between 7 and 14 more preferred, and those between 9 and 13 most preferred. Examples of such nonionic surfactants are PEG-60 corn glycerides, PEG-20 sorbitan monostearate, phenoxy-poly(ethyleneoxy)ethanol, sorbitan monooleate, and the like. Especially preferred are compendial surfactants such as those described in compendia such as the Food Chemicals Codex, National Formulary, U.S. Pharmacopeia, and the Code of Federal Regulations. It is preferred that the average diameter of the droplets of the emulsion be from about 50 nanometers (nm) to about 20 micrometers (μm) and more preferably from about 200 nm to about 5 μm. In general each surfactant is present in an amount no greater than about 2 wt. % of the composition and more generally no greater than about 1 wt. % of the composition. Also, it is important to prefer the nature of the side-chains of the surfactants to those with no double bonds, and this invention is most preferred to include those without unsaturated carbon-carbon bonds. The reason for this is that unsaturated fatty acid side chains (called also "olefinic" fatty acids) tend to oxidize over time, rendering them unsuitable. They tend to become colored, or dark, and give rise to intermediates that may react with the important peptide in the same formulation, rendering it less useful or unsuitable from a regulatory vantage point (in the US, for example, the key regulatory body being the FDA, and in other countries its counterpart). Olefins are suspected to have the additional liability of contributing to irritation which must be avoided for intranasal applications. However, unsaturated side-chain surfactants are not excluded from use in this invention. For example, polysorbate 80, containing a monounsaturated side chain of oleic acid ester, may be mitigated in its irritation liability by using a limited concentration of same, generally under 1% in the formulation, or by adding soothing components, such as glycerin, to the formulation to negate such undesired effect.

In one preferred embodiment, the emulsified or discontinuous phase that contains the permeation enhancer is in the form of droplets. In general, smaller droplets confer greater stability. Larger droplets may cause instability and may decrease shelf-life. In preferred embodiments the lipid droplet size ranges from 0.025 microns (25 nm) to 20 microns and preferably from 0.1 microns to 5 microns.

In one embodiment of the present invention, the composition comprises a pharmaceutically-effective amount of a reproductive hormone peptide capable of treating prostate cancer or relieving the symptoms of fibrosis or endometriosis. Essentially any suitable reproductive hormone peptide can be used, including, for example, luteinizing hormone (LH) and its analogs, follicle-stimulating hormone (FSH) and its analogs, and gonadotropin-releasing hormone (GnRH—also known as luteinizing hormone releasing hormone (LHRH)) and its analogs, for example, goserelin, nafarelin, buserelin, and leuprolide. Examples of suitable reproductive hormone peptides are described also in K. Saeb-Parsy, et al., Instant Pharmacology, 57-62 (1999). LHRH-Lamprey III and closely related analogs thereof are particularly preferred because of their relatively high activity. Yu et al., PNAS, 94: 9499 (1997).

In still another embodiment of the present invention, the composition comprises a pharmaceutically-effective amount of an opioid peptide or peptidomimetic (synthetic peptide) capable of reducing pain. Essentially any suitable opioid peptide or peptidomimetic may be employed. Examples of suitable opioid peptides include enkephalins, endorphins, exorphins, dynorphins, endomorphins, syndyphalins, BAM peptides, metorphamide, and valorphin. Shorter peptides are preferred, with especially potent shorter peptides such as, for example, the endomorphins being particularly preferred. For use in an emulsion of the present invention, opiate alkaloids of the morphine class are preferred because the free bases of such alkaloids are capable of stabilizing emulsions formed using acidic emulsifying agents. This functions to stabilize the resulting emulsion without the need for further pH modifiers. Examples of such opiate alkaloids are morphine, codeine, oxycodone, hydrocodone, hydromorphone, fentanyl, sufentanil, levorphanol, meperidine, methadone, and the like.

Yet another embodiment of the present invention is a composition which comprises a pharmaceutically-effective amount of an anti-obesity agent which is capable of alleviating a disorder which causes obesity in mammals, particularly humans. Essentially any suitable anti-obesity agent may be employed. Examples of such agents include galanins, bombesin, incretins such as glucagon and glucagon-like peptides, insulin-like growth factors, leptins, melanotropin, peptides which interact with the melanocortin receptor, and analogs thereof. Glucagon and glucagon-like peptides are preferred, with GLP-1 being particularly preferred. Leptins are also preferred, with leptin fragments, such as leptin 22-56 (obese gene peptide), being particularly preferred. Peptides which interact with the melanocortin receptor such as, for example, alpha-MSH and their analogs, are preferred (such peptides have been reported to decrease appetite. Science, 291: 1691 (2001)).

A further embodiment of the present invention is a composition which comprises a pharmaceutically-effective amount of an appetite-enhancing peptide which is capable of increasing appetite in mammals, preferably humans. Essentially any suitable appetite-enhancing compound may be employed. Examples of such appetite-enhancing compounds include compounds which serve as antagonists of the aforementioned anti-obesity agents. Science, 291: 1691 (2001).

A further embodiment of the present invention is the addition to the formulation of an enzyme inhibitor. As is well known to practitioners in peptide and protein biochemistry, peptides tend to be very sensitive to the presence of enzymes, such as proteolytic enzymes, that rapidly degrade the peptide when present in even minute amounts. Typical enzyme inhibitors that are commonly employed and that may be incorporated into the present invention include, but are not limited to leupeptin, aprotinin, and the like.

The composition of the present invention may exist in various forms, for example, an oil-in-water emulsion, a water-in-oil emulsion, and a water-in-oil-in-water emulsion. The active compounds of the compositions of the present invention may exist in either the continuous or the dispersed phase or in both phases depending upon whether the compounds are hydrophilic, lipophilic, or amphiphilic. In an example of a preferred embodiment of the present invention, the emulsion comprises oil droplets dispersed in a continuous aqueous phase with a lipophilic enhancer being contained in the oil droplets and a water-soluble pharmaceutically-active compound dissolved in the continuous aqueous phase. In a preferred embodiment wherein an oil phase is utilized, the concentration of the oil in the oil phase is such that it does not promote crystallization.

In some instances the permeation enhancers used in the instant invention may crystallize at room temperature or at higher temperatures. In order to inhibit or prevent such crystallization, in a preferred embodiment the composition includes one or more crystallization inhibitors to inhibit the crystallization of the permeation enhancer. Crystallization, if allowed to proceed, renders the emulsion unstable and has an adverse effect on shelf life. Preferred crystallization inhibitors function by lowering the temperature at which the involved compound crystallizes. Examples of such crystallization inhibitors include natural oils, oily substances, waxes, esters, and hydrocarbons. Examples of natural oils or oily substances include Vitamin E acetate, octyl palmitate, sesame oil, soybean oil, safflower oil, avocado oil, palm oil, and cottonseed oil. The selection of a suitable crystallization inhibitor is deemed to be within the scope of those skilled in the art from the teachings herein. Preferred crystallization inhibitors function by lowering the temperature at which the permeation enhancer crystallizes.

Inhibitors which are capable of lowering the temperature of crystallization of the involved compound to below about 25° C. are particularly preferred, with those capable of lowering the crystallization of the involved compound to below about 5° C. being especially preferred. Examples of especially preferred crystallization inhibitors for use in inhibiting the crystallization of oxacyclohexadecan-2-one include hexadecane, isopropyl myristate, octyl palmitate, cottonseed oil, safflower oil, and Vitamin E acetate, each of which may be used in pharmaceutical preparations.

The crystallization inhibitor is present in the composition in a concentration effective to inhibit the crystallization of the permeation enhancer. In general the crystallization inhibitor is present in an amount of about 0.001 to about 5 wt. % of the composition, and more generally in an amount of from about 0.01 to about 2 wt % of the composition. In one embodiment the crystallization inhibitor is present in an amount of from about 0.1 to about 1 wt. % of the composition. The crystallization inhibitor is one preferably used when the enhancer has a crystallization temperature above about 0 degrees Centigrade. In particular, for example, a crystallization inhibitor is preferably used when the enhancer is, pentadecalactone and/or cyclohexadecanone, since these crystallize above room temperature.

The composition of the present invention is delivered through a nasal spray applicator. If intra-nasal application is desired, the composition may be placed in an intra-nasal spray-dosing device or atomizer and may be applied by spraying it into the nostrils of a patient for delivery to the mucous membrane of the nostrils. A sufficient amount is applied to achieve the desired systemic or localized drug levels. For an intra-nasal spray, up to about 200 microliters is typically applied, with an application of about 50 to about 150 microliters being preferred, and 75 to 120 microliters most preferred. One or more nostrils may be dosed and application may occur as often as desired or as often as is necessary. In preferred embodiments, the nasal spray applicator is selected to provide droplets of the composition of a mean size of from about 10 microns to about 200 microns. More generally the droplet size is from about 30 microns to about 100 microns.

The pharmaceutically active peptide spray composition of the invention is generally employed in a dosing regimen that is dependent on the patient being treated. Thus the frequency of the use and the amount of the dose may vary from patient to patient. In general, dosing is in an amount (the amount internalized after absorption from the mucosa) of from about 0.05 mg to about 10 mg and the frequency of dose is 3 to 4 times per day. This will vary with the potency of each peptide in question. As known in the art, the treatment of a disease varies from patient to patient, and based on known pharmaceutically active peptide therapies and the teachings herein one skilled in the art can select the dosing regimen and dosage for a particular patient or patients.

The composition of the present invention comprises a pharmaceutically active peptide. The pharmaceutically active peptide is present in the composition in a therapeutically-effective amount. In general the pharmaceutically active peptide is present in an amount of about 0.005 to about 10 wt. % of the composition, and more generally an amount of about 0.01 to about 5 wt. % of the composition. In one embodiment the pharmaceutically active peptide is present in an amount of about 0.1 to about 2 wt. % of the composition.

Although a preferred embodiment is a preformulated composition, it is also within the scope of the present invention that a patient may be treated with the hereinabove-described and hereinbelow-described combination that is not preformulated; i.e., the pharmaceutically active peptide in liquid carrier and the enhancer may be mixed at the time of application, such as where the mixing occurs in an atomizer at the time the composition is sprayed.

EXAMPLES

The Examples below are illustrative of compositions of the present invention. The concentrations of the ingredients comprising the compositions are given in percent by weight relative to the total weight of the composition.

Example Nos. 1 & 2 are examples of compositions of the present invention for use in an intra-nasal spray.

In Example Nos. 1, the ingredients of Part A were mixed by mechanically stirring at 40° C. until homogeneous. The ingredients of Part B were mixed separately using magnetic stirring at 40° C. until homogeneous and then added to Part A. The resulting mixture was stirred vigorously and Part C was added slowly to the mixture. Following the addition of Part C. Part D was added and the resulting mixture was stirred for 4 hours at 40° C. The mixture was allowed to cool to room temperature while stirring for an additional 18 hours. Part E was then added while shaking and stirring for 4 hours. The resulting mixture is referred to as the "Premix".

A solution of pharmaceutically-active compound in the concentration desired was prepared separately. The pharmaceutically-active compound was mixed with and dissolved in water by agitating until homogeneous. A pH modifier was then added and the resulting mixture was mixed by rolling on a roller mill at 120 rpm at room temperature until the solution was homogeneous.

The Premix was added to the aqueous solution of pharmaceutically-active compound at room temperature and the resulting mixture was mixed by rolling on a roller mill at 120 rpm until the final mixture composition was homogeneous.

Example No. 1

This example describes the preparation of a composition which can be used as an intra-nasal spray for the delivery of GHRP-6 (H-His-D-Trp-Ala-Trp-D-Phe-Lys-$NH_2$).

| Premix | Wt % |
|---|---|
| Part A | |
| oxacyclohexadecan-2-one (Firmenich) - enhancer | 2.00% |
| cottonseed oil, super refined (Croda) - solvent, crystallization inhibitor | 0.67% |
| petrolatum - Protopet (Witco) - solvent, Ostwald-ripening inhibitor | 0.14% |
| Part B | |

-continued

| Premix | Wt % |
|---|---|
| propylene glycol, USP - solvent | 1.00% |
| glycerin, USP - cosolvent, emollient, humectant and protein stabilizer | 2.00% |
| water, sterile and deionized | 44.05% |
| Part C | |
| acrylates/$C_{10-30}$ alkyl acrylate crosspolymer - Pemulen TR2, NF grade (Noveon, Inc.) - emulsifier and thickener | 0.10% |
| Part D | |
| benzalkonium chloride, 50% aqueous solution - Maquat (Mason) - preservative | 0.01% |
| Part E | |
| triethanolamine, NF - pH modifier | 0.03% |

Solution of Pharmaceutically-active Compound

| | |
|---|---|
| water, sterile and deionized | 49.10% |
| GHRP-6 (Bachem) - pharmaceutically-active compound | 0.87% |
| triethanolamine, NF - pH modifier | 0.03% |

The resulting composition comprised a stable emulsion in which the dispersed phase consisted of liquid droplets which were uniformly dispersed in the composition and which consisted of the enhancer dissolved in the solvents comprising the crystallization inhibitor and the Ostwald-ripening inhibitor. The continuous phase comprised an aqueous solution of propylene glycol, glycerin, preservative, and pharmaceutically-active compound. The pH modifier was considered to be associated with the emulsifier. One hundred microliters of the composition contained approximately 100 micrograms of GHRP-6.

Example No. 2

This example describes the preparation of a composition which can be used as an intra-nasal spray for the delivery of oxycodone. Oxycodone was used in the form of its free base prepared from the commercially available hydrochloride salt by dissolving in 20 parts of water and a stoichiometric amount of 1.0 N sodium hydroxide. The precipitate was collected and washed with water. The precipitate was then dried at room temperature using a vacuum pump.

Oxycodone Intra-nasal Preparation

| | Wt % |
|---|---|
| Part A | |
| oxacyclohexadecan-2-one (Firmenich) - enhancer | 2.00% |
| cottonseed oil, super refined (Croda) - solvent, crystallization inhibitor | 0.67% |
| petrolatum - Protopet (Witco) - solvent, Ostwald-ripening inhibitor | 0.14% |
| oxycodone, free base - pharmaceutically-active compound | 2.00% |
| Part B | |
| acrylates/$C_{10-30}$ alkyl acrylate crosspolymer - Pemulen TR2, NF Grade (Noveon, Inc.) - emulsifier and thickener | 0.08% |

-continued

| | Wt % |
|---|---|
| Part C | |
| glycerin, USP - cosolvent, emollient, humectant and protein stabilizer | 2.10% |
| water, sterile and deionized | 93.00% |
| benzalkonium chloride, 50% aqueous solution - Maquat (Mason) - preservative | 0.01% |

The ingredients of Part A were combined at 40° C. by mechanical stirring until a paste was formed. Part B was then combined with Part A by mechanically stirring at 40° C. until a homogeneous paste was formed. Part C was then added and the resulting mixture was stirred mechanically at room temperature until a white homogeneous emulsion was formed.

The free base of oxycodone, which is insoluble in water, is strong enough to stabilize emulsions formed using acrylates/$C_{10-30}$ alkyl acrylate emulsifier. This enables the composition to exist in the form of a cohesive homogeneous emulsion without the need for use of further pH modifiers and in order to avoid the formation of an inorganic salt. The dispersed phase consisted of the enhancer dissolved in the solvents comprising the crystallization inhibitor and the Ostwald-ripening inhibitor. The continuous phase consisted of glycerin, preservative, and water. The pharmaceutically-active compound was considered to be associated with the acrylates/$C_{10-30}$ alkyl acrylate crosspolymer emulsifier.

One hundred microliters of the composition contained approximately 2 milligrams of oxycodone.

We claim:

1. A pharmaceutical composition in the form of an emulsified nasal spray comprising: a macrocyclic permeation enhancer, a liquid carrier comprising water, an emulsifying agent, and a therapeutically effective amount of a pharmaceutically active agent other than insulin selected from the group consisting of peptides, peptidomimetics, and proteins; wherein said pharmaceutical composition is free of a hydrocolloid emulsifier; and wherein said macrocyclic permeation enhancer is a Hsieh enhancer emulsified in the liquid carrier; said Hsieh enhancer having the following structure:

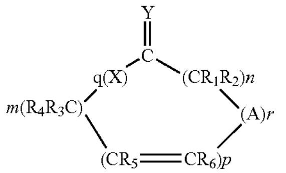

wherein X is oxygen, sulfur or an imino group of the structure

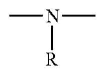

and wherein Y is oxygen, sulfur or an imino group of the structure

=N—R.

with the proviso that when Y is the imino group, S is an imino group, and when Y is sulfur, X is sulfur or an imino group, A is a group having the structure

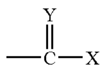

wherein X and Y are defined above, m and n are integers having a value from 1 to 20 and the sum of m+n is not greater than 25, p is an integer having a value of 0 or 1, q is an integer having a value of 0 or 1, r is an integer having a value of 0 or 1, and each of R, $R_1$, $R_2$, $R_3$, $R_4$, $R_5$ and $R_6$ is independently hydrogen or an alkyl group having from 1 to 6 carbon atoms which may be straight chained or branched provided that only one of $R_1$ to $R_6$ can be an alkyl group, with the proviso that when p, q and r have a value of 0 and Y is oxygen, mtn is at least 11, and with the further proviso that when X is an imino group, q is equal to 1, Y is oxygen, and p and r are 0, then m+n is at least 11.

2. The pharmaceutical composition of claim 1, wherein said Hsieh enhancer is cyclopentadecalactone or cyclohexadecanone.

3. The pharmaceutical composition of claim 1, further comprising a crystallization inhibitor.

4. The pharmaceutical composition of claim 1, further comprising an enzyme inhibitor.

5. The pharmaceutical composition of claim 4, wherein said enzyme inhibitor is selected from the group consisting of leupeptin and aprotinin.

6. The pharmaceutical composition of claim 1, wherein said pharmaceutical composition is formulated in a manner suitable to be administered for use in treating chronic conditions.

7. A method for treating a patient with a peptide, a peptidomimetic, or a protein, said method comprising administering to a patient in need of peptide treatment, peptidomimetic treatment, or protein treatment, a pharmaceutical composition in the form of an emulsified nasal spray comprising: a macrocyclic permeation enhancer, a liquid carrier comprising water, an emulsifying agent, and a therapeutically effective amount of a pharmaceutically active agent other than insulin selected from the group consisting of peptides, peptidomimetics, and proteins; wherein said pharmaceutical composition is free of a hydrocolloid emulsifier; and wherein said macrocyclic permeation enhancer is a Hsieh enhancer emulsified in the liquid carrier; said Hsieh enhancer having the following structure:

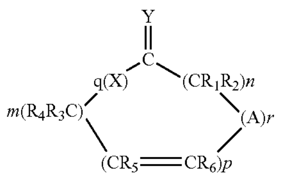

wherein X is oxygen, sulfur or an imino group of the structure

and wherein Y is oxygen, sulfur or an imino group of the structure

=N—R with the proviso that when Y is the imino group, X is an imino group, and when Y is sulfur, X is sulfur or an imino group, A is a group having the structure

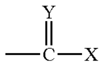

wherein X and Y are defined above, m and n are integers having a value from 1 to 20 and the sum of m+n is not greater than 25, p is an integer having a value of 0 or 1, q is an integer having a value of 0 or 1, r is an integer having a value of 0 or 1, and each of R, $R_1$, $R_2$, $R_3$, $R_4$, $R_5$ and $R_6$ is independently hydrogen or an alkyl group having from 1 to 6 carbon atoms which may be straight chained or branched provided that only one of $R_1$ to $R_6$ can be an alkyl group, with the proviso that when p, q and r have a value of 0 and Y is oxygen, m+n is at least 11, and with the further proviso that when X is an imino group, q is equal to 1, Y is oxygen, and p and r are 0, then m+n is at least 11.

8. The method of claim 7, wherein said Hsieh enhancer is cyclopentadecalactone or cyclohexadecanone.

9. The method of claim 7, wherein said pharmaceutical composition further comprises a crystallization inhibitor.

10. The method of claim 7, wherein said pharmaceutical composition further comprises an enzyme inhibitor.

11. The method of claim 10, wherein said enzyme inhibitor is selected from the group consisting of leupeptin and aprotinin.

12. The method of claim 7, wherein said pharmaceutical composition is formulated in a manner suitable to be administered for use in treating chronic conditions.

13. The pharmaceutical composition of claim 1, wherein said emulsifying agent is selected from the group consisting of: surfactants that are free of carbon-carbon double bonds and mixtures or such surfactants.

14. The pharmaceutical composition of claim 13, wherein said surfactant(s) is/are non-ionic.

15. The method of claim 7, wherein said emulsifying agent is selected from the group consisting of: surfactants that are free of carbon-carbon double bonds and mixtures of such surfactants.

16. The method of claim 15, wherein said surfactant(s) is/are non-ionic.

* * * * *